(12) United States Patent
Shindo

(10) Patent No.: US 10,531,855 B2
(45) Date of Patent: Jan. 14, 2020

(54) X-RAY COMPUTED TOMOGRAPHY APPARATUS

(71) Applicant: Toshiba Medical Systems Corporation, Otawara-shi (JP)

(72) Inventor: Yasutaka Shindo, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 196 days.

(21) Appl. No.: 15/854,972

(22) Filed: Dec. 27, 2017

(65) Prior Publication Data

US 2018/0177478 A1 Jun. 28, 2018

(30) Foreign Application Priority Data

Dec. 28, 2016 (JP) .................................. 2016-255340
Dec. 25, 2017 (JP) .................................. 2017-247862

(51) Int. Cl.
*A61B 6/00* (2006.01)
*A61B 6/03* (2006.01)
*A61B 6/04* (2006.01)

(52) U.S. Cl.
CPC ............... *A61B 6/54* (2013.01); *A61B 6/032* (2013.01); *A61B 6/0407* (2013.01); *A61B 6/40* (2013.01); *A61B 6/4266* (2013.01); *A61B 6/481* (2013.01)

(58) Field of Classification Search
CPC ......... A61B 6/54; A61B 6/032; A61B 6/0407; A61B 6/40; A61B 6/4266; A61B 6/481

USPC ...................................................... 378/4–20
See application file for complete search history.

(56) References Cited

U.S. PATENT DOCUMENTS

| | | | |
|---|---|---|---|
| 6,426,996 | B1 | 7/2002 | Moribe et al. |
| 2011/0019793 | A1 | 1/2011 | Honda et al. |
| 2012/0132822 | A1 | 5/2012 | Okada |

FOREIGN PATENT DOCUMENTS

| | | |
|---|---|---|
| JP | 10-71141 | 3/1998 |
| JP | 2001-137223 | 5/2001 |
| JP | 2001-309914 | 11/2001 |
| JP | 2003-102716 | 4/2003 |
| JP | 2011-24806 | 2/2011 |
| JP | 2012-130656 | 7/2012 |
| JP | 2017-64392 | 4/2017 |

*Primary Examiner* — Courtney D Thomas
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, an X-ray detector, acquisition circuitry, a high voltage generator, and processing circuitry. The acquisition circuitry acquires electrical signals from a plurality of X-ray detection elements, and bundles the electrical signals in bundle units in accordance with a resolution mode of the X-ray detector. The processing circuitry determines a resolution mode, an application dose condition, and an X-ray exposure time for target CT imaging. The processing circuitry determines the focus size for the target CT imaging based on the determined resolution mode, application dose condition, and X-ray exposure time.

5 Claims, 15 Drawing Sheets

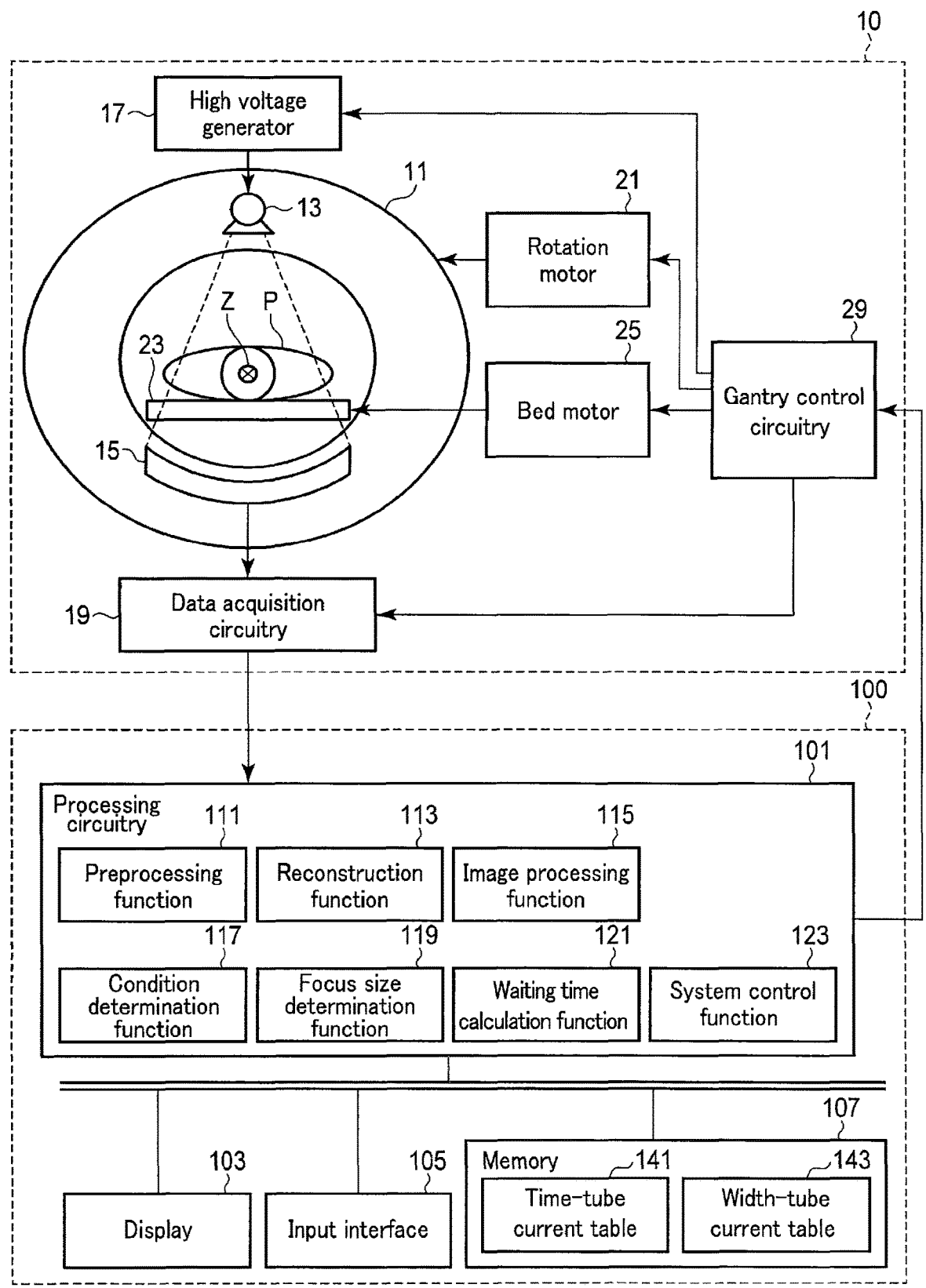
F I G. 1

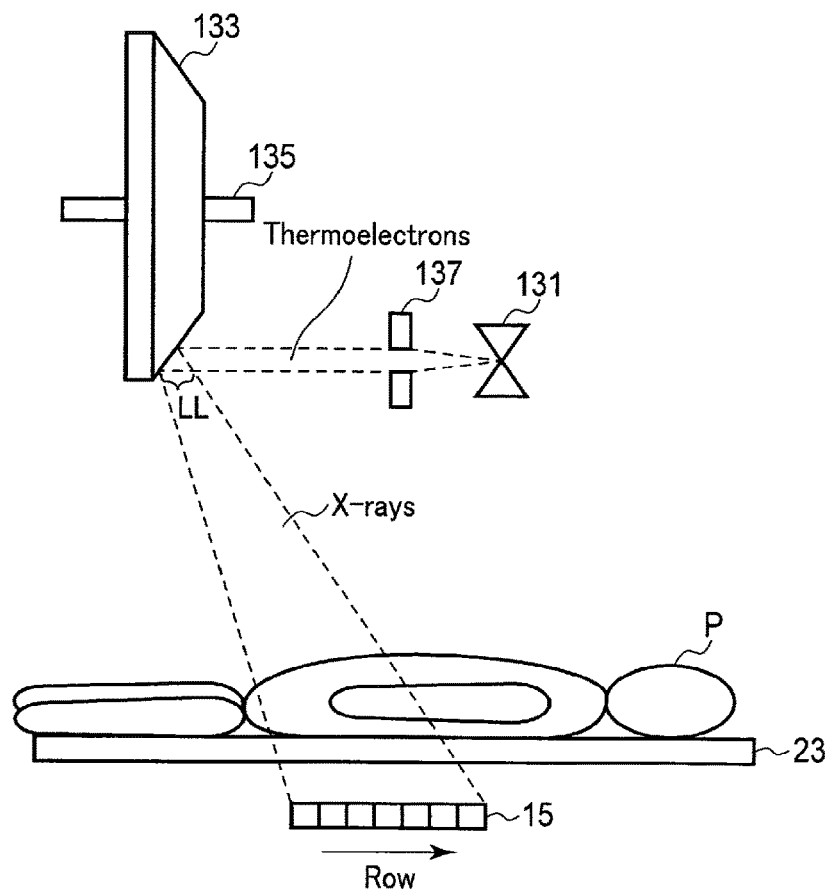
F I G. 4
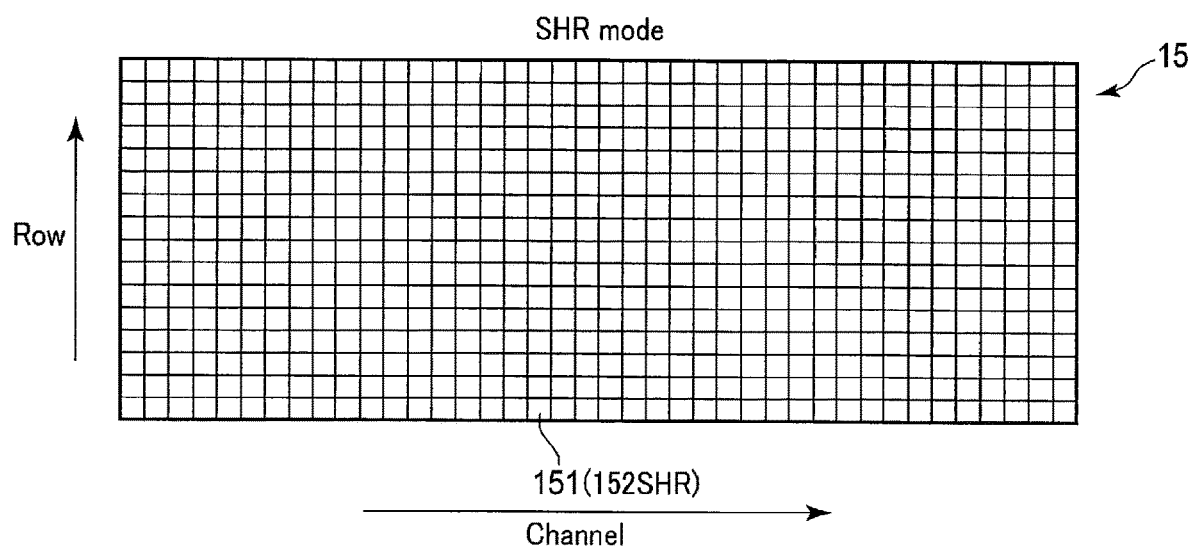
F I G. 5

| Resolution mode | Part (FOV) | Physique/SD | | | | | | |
|---|---|---|---|---|---|---|---|---|
| | | kVp | Maximum mA → Time | | | | | |
| SHR: nSL × mCH | S,M,L | V5–V10 | S2 | S1 | L3 | L2 | | |
| HR: 2nSL × mCH | S | V4–V10 | S2 | S1 | L3 | L2 | L1 | |
| | M,L | V5–V10 | S2 | S1 | L3 | L2 | L1 | |
| Normal: 2nSL × m/2CH | S,M,L | V3–V10 | S2 | S1 | L3 | L2 | L1 | L0 |
F I G. 11
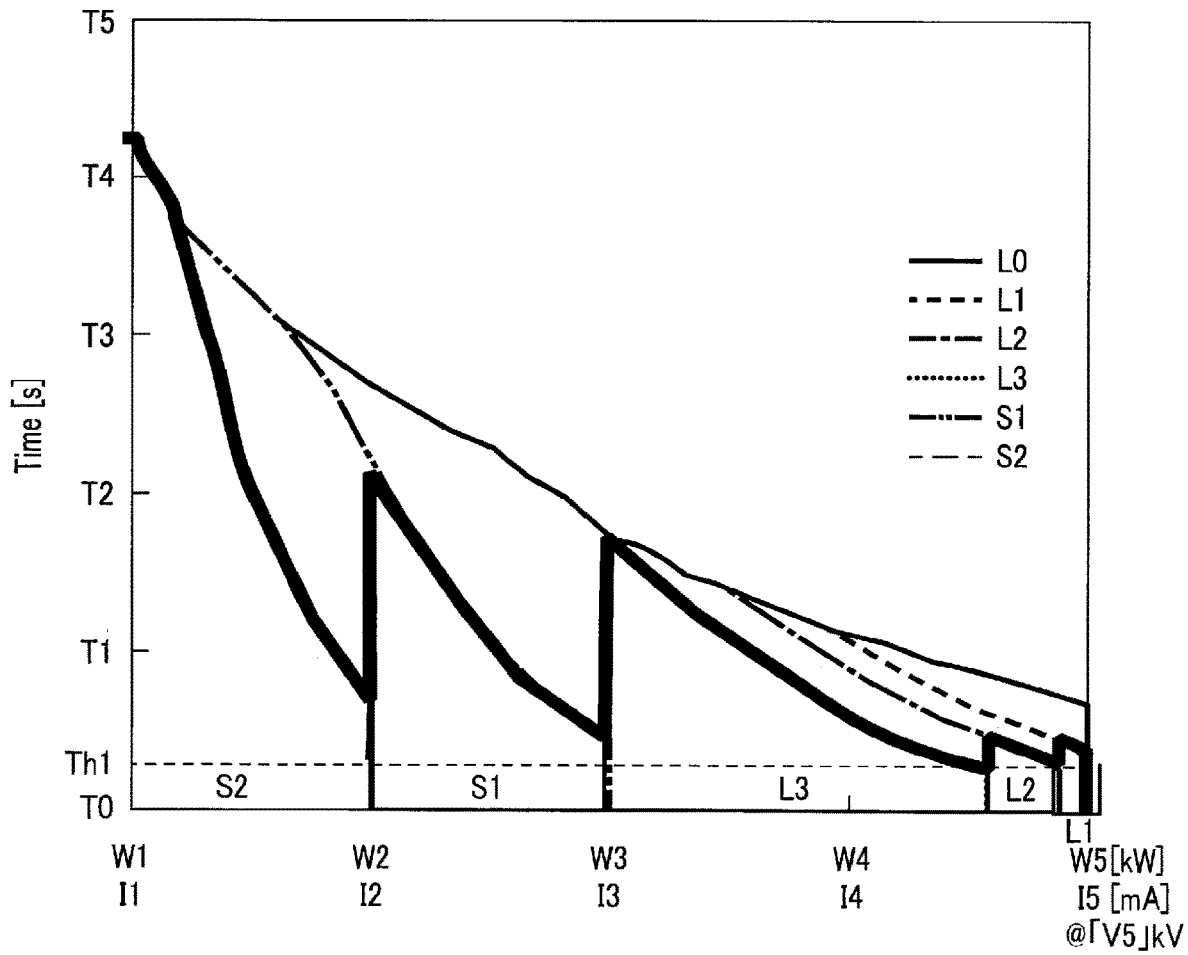
F I G. 12

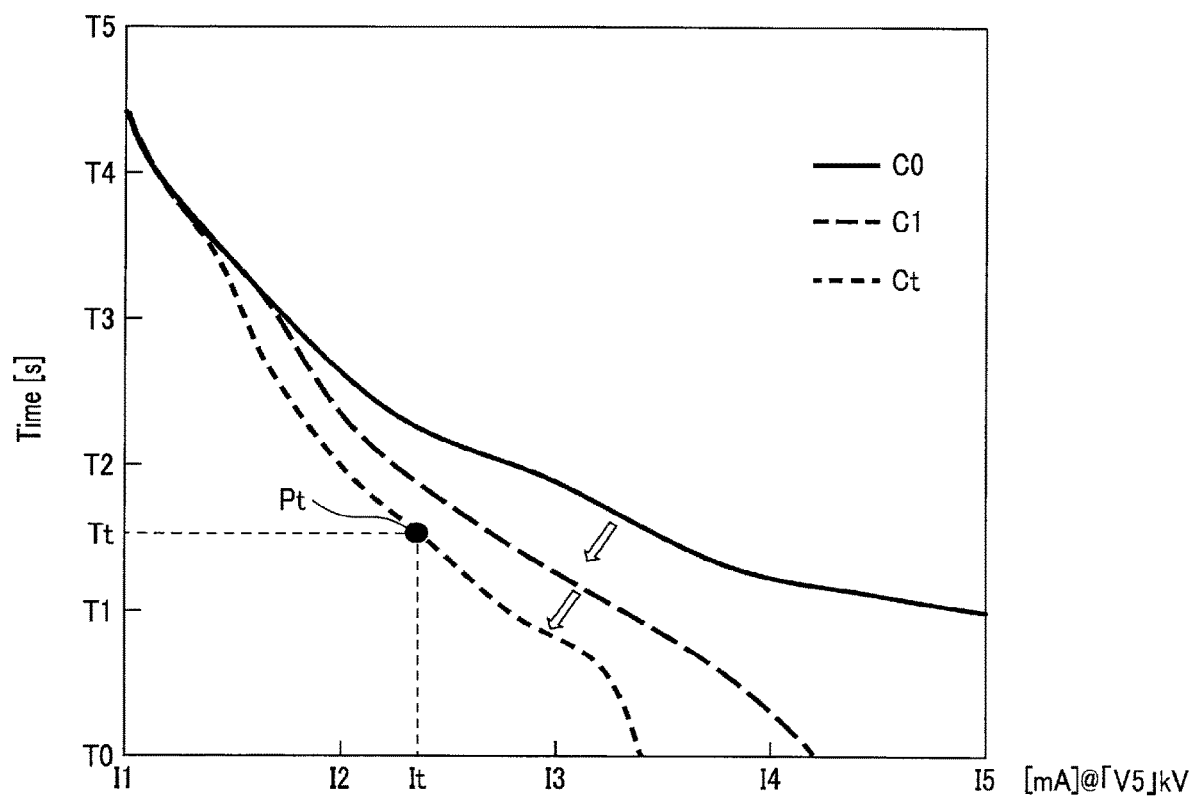
F I G. 18

X-RAY COMPUTED TOMOGRAPHY APPARATUS

CROSS-REFERENCE TO RELATED APPLICATIONS

This application is based upon and claims the benefit of priority from the Japanese Patent Application No. 2016-255340, filed Dec. 28, 2016 and the Japanese Patent Application No. 2017-247862, filed Dec. 25, 2017, the entire contents of all of which are incorporated herein by reference.

FIELD

Embodiments described herein relate generally to an X-ray computed tomography apparatus.

BACKGROUND

In X-ray computed tomography apparatuses, the technique of switching a focus size of X-rays in accordance with a set tube current value has been used. As X-ray detection elements of an X-ray detector have been downsized, a high resolution mode or a super high resolution mode in which a reading channel pitch is shorter in the channel direction or in the row direction in comparison with a normal resolution mode has been realized. However, in the case where the focus size is switched in accordance with the set tube current value, the channel pitch is not taken into consideration, and accordingly, there may be a case where CT imaging cannot be performed with an optimal focus size for a designated resolution mode.

BRIEF DESCRIPTION OF THE DRAWINGS

FIG. 1 illustrates the configuration of an X-ray computed tomography apparatus according to the present embodiment.

FIG. 4 is a schematic view of a focus size according to the present embodiment in which an anode is viewed from the side direction.

FIG. 5 is a plane view of X-ray detection elements of an X-ray detector according to the present embodiment in which reading channels of the X-ray detector in a super high resolution mode are schematically illustrated.

FIG. 11 is an example of an imaging condition table used by processing circuitry shown in FIG. 1.

FIG. 12 is a graph showing the time-tube current relationship under conditions of example 1.

FIG. 18 is a schematic diagram of a procedure of a determination algorithm for a width and a length of a focus according to a modification.

DETAILED DESCRIPTION

Figure 2:
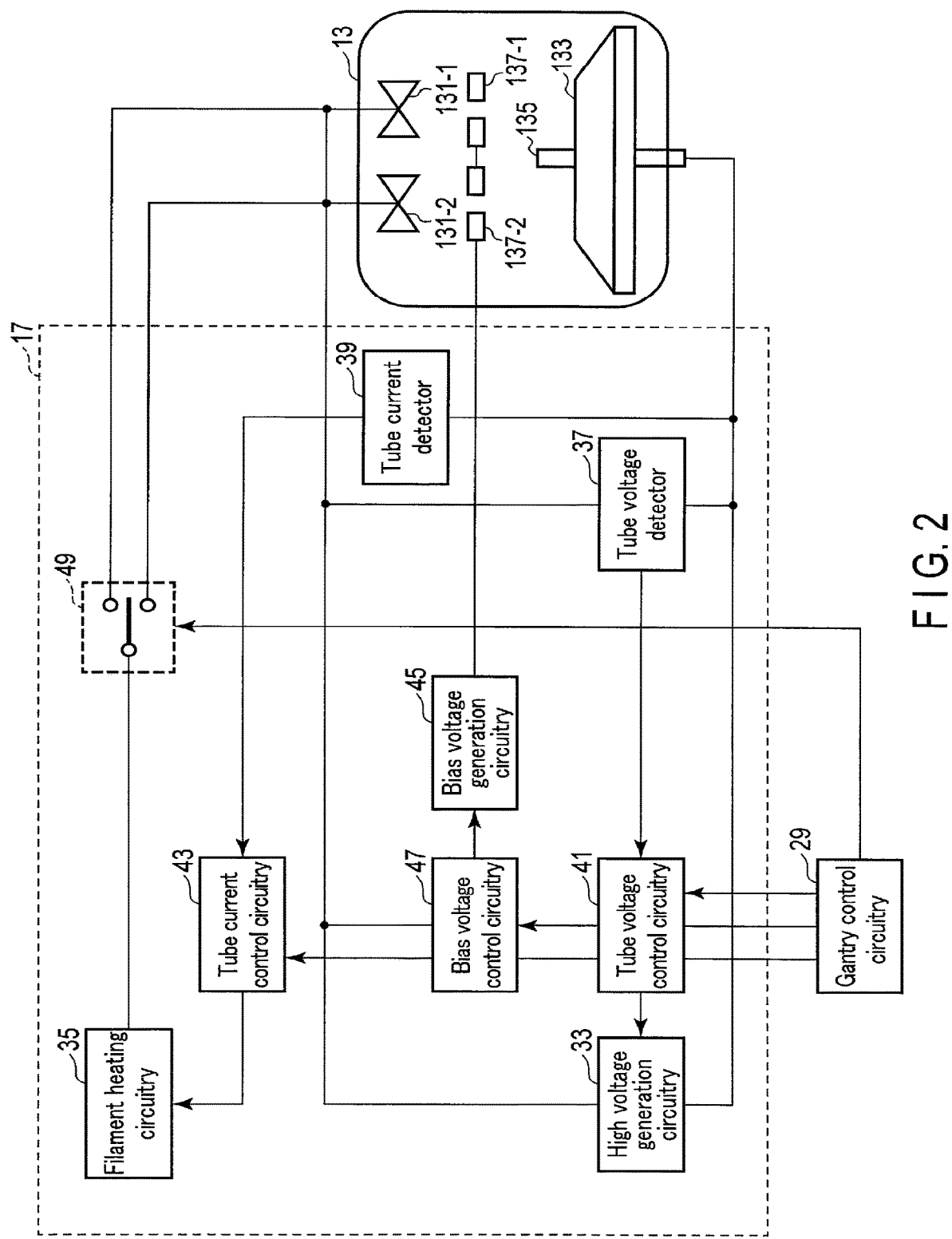
FIG. 2 illustrates the configuration of an X-ray tube and a high voltage generator shown in FIG. 1.

An X-ray computed tomography apparatus according to the present embodiment includes an X-ray tube, an X-ray detector, acquisition circuitry, a high voltage generator, and processing circuitry. The X-ray tube generates X-rays. The X-ray detector comprises a plurality of X-ray detection elements that detect X-rays. The acquisition circuitry acquires electrical signals from the plurality of X-ray detection elements and bundles the acquired electrical signals in bundle units in accordance with a resolution mode of the X-ray detector. The high voltage generator controls the dose and the focus size of the X-ray tube. The processing circuitry determines a resolution mode, an application dose condition, and an X-ray exposure time for target CT imaging. The processing circuitry determines the focus size for the target CT imaging based on the determined resolution mode, application dose condition, and X-ray exposure time.

In the following, the X-ray computed tomography apparatus according to the present embodiment will be explained with reference to the drawings.

FIG. 1 shows the configuration of the X-ray computed tomography apparatus according to the present embodiment. As shown in FIG. 1, the X-ray computed tomography apparatus of the present embodiment includes a gantry 10 and a console 100. For example, the gantry 10 is placed in a CT examination room, and the console 100 is placed in a control room adjacent to the CT examination room. The gantry 10 and the console 100 are communicatably connected to each other. The gantry 10 includes an imaging mechanism configured to perform X-ray CT imaging of a subject P. The console 100 is a computer that controls the gantry 10.

As shown in FIG. 1, the gantry 10 includes a rotation frame 11 of an essentially cylindrical shape, which includes a bore. The rotation frame 11 is also referred to as a rotation unit. As shown in FIG. 1, an X-ray tube 13 and an X-ray detector 15 which are arranged to face each other via the bore are attached to the rotation frame 11. The rotation frame 11 is a metal frame made, for example, of aluminum, in an annular shape. As will be detailed later, the gantry 10 includes a main frame made of metal, such as aluminum. The main frame is also referred to as a stationary unit. The rotation frame 11 is rotatably supported by the main frame.

The X-ray tube 13 generates X-rays. The X-ray tube 13 is connected to a high voltage generator 17 via a high voltage cable. The high voltage generator 17 is attached, for example, to the rotation frame 11. The high voltage generator 17 adjusts the dose to be applied to the X-ray tube 13

(i.e., tube voltage and tube current) and the focus size of the X-rays in accordance with control by the gantry control circuitry 29.

FIG. 2 shows the configuration of the X-ray tube 13 and the high voltage generator 17 according to the present embodiment. As shown in FIG. 2, the X-ray tube 13 houses a first cathode 131-1, a second cathode 131-2, an anode 133, a rotor 135, a first grid electrode 137-1, and a second grid electrode 137-2. In the following description, the first cathode 131-1 and the second cathode 131-2 are referred to as a cathode 131 when they are not distinguished, and the first grid electrode 137-1 and the second grid electrode 137-2 are referred to as a grid electrode 137 when they are not distinguished. The first cathode 131-1 and the second cathode 131-2 each have a filament made of metal such as tungsten, nickel, etc. in a narrow linear shape. The first cathode 131-1 and the second cathode 131-2 are connected to the high voltage generator 17 through a cable, etc. The first cathode 131-1 and the second cathode 131-2 each generate heat and emit thermoelectrons upon receiving a filament heating current supplied from the high voltage generator 17. The first cathode 131-1 and the second cathode 131-2 are different in length. In the following description, it is assumed that the first cathode 131-1 is longer than the second cathode 131-2.

The anode 133 is an electrode made of a heavy metal such as tungsten or molybdenum in a disc shape. The rotor 135 is attached to the anode 133. The anode 133 rotates as the rotor 135 rotates about its axis. The anode 133 and the rotor 135 form a rotating anode. The high voltage generator 17 applies a high voltage between the cathode 131 and the anode 133.

The grid electrode 137 is arranged between the cathode 131 and the anode 133. The grid electrode 137 electrically or magnetically regulates the focus size on the surface of the anode 133. The grid electrode 137 deflects the trajectory of the thermoelectrons traveling from the cathode 131 to the anode 133 and regulates the focus size upon receiving a voltage applied from the high voltage generator 17.

Figure 3:
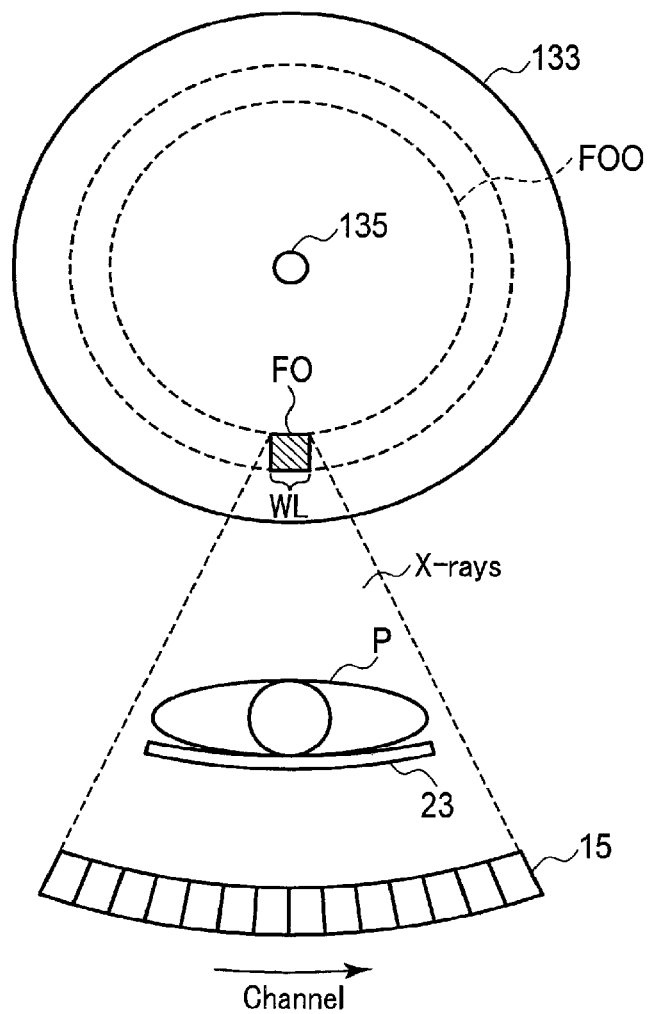
FIG. 3 is a schematic view of a focus size according to the present embodiment in which an anode is viewed from a cathode side.

FIGS. 3 and 4 each are a schematic view of the focus size. FIG. 3 shows the anode 133 viewed from the cathode 131 side, and FIG. 4 is the anode 133 viewed from the side direction. As shown in FIGS. 3 and 4, the thermoelectrons emitted from the cathode 131 travel directed toward the anode 133 by the tube voltage applied between the cathode 131 and the anode 133. In this case, the thermoelectrons are converged as a beam by a bias voltage applied to the grid electrode 137. The anode 133 emits bremsstrahlung X-rays upon receiving the thermoelectrons from the cathode 131. A portion where the X-rays impinge on the anode 133 is referred to as a focus FO. The focus FO forms a ring-shaped path FOO as the anode 133 rotates. The length in a channel direction of the focus FO is defined as a width WL, and the length in a row direction of the focus FO is defined as a length LL. The width WL is essentially parallel to the channel direction of the X-ray detector 15, and accordingly contributes to the resolution within a slice plane. The width WL is actively controlled by the grid electrode 137. The length LL is essentially parallel to the row direction of the X-ray detector 15, and accordingly contributes to the resolution in the row direction, namely, in the body axis direction of the subject P. The length LL is not actively controlled by the grid electrode 137, but slightly varies due to control of the width by the grid electrode 137.

As shown in FIG. 2, the high voltage generator 17 applies a high voltage to the X-ray tube 13 in accordance with control by the gantry control circuitry 29, and supplies a filament heating current. Specifically, the high voltage generator 17 includes high voltage generation circuitry 33, filament heating circuitry 35, a tube voltage detector 37, a tube current detector 39, tube voltage control circuitry 41, tube current control circuitry 43, bias voltage generation circuitry 45, and bias voltage control circuitry 47.

The high voltage generation circuitry 33 generates a high voltage to be applied to the X-ray tube 13 in accordance with control by the tube voltage control circuitry 41. The high voltage generation circuitry 33 and the anode 133 are connected by an anode side high voltage cable, and the high voltage generation circuitry 33 and the cathode 131 are connected by a cathode side high voltage cable. The high voltage generation circuitry 33 may adopt any type of high voltage generator such as a transformer type X-ray high voltage generator, a constant voltage type X-ray high voltage generator, a capacitor type X-ray high voltage generator, or an inverter type X-ray high voltage generator.

The filament heating circuitry 35 generates power to heat the cathode 131 in accordance with control by the tube current control circuitry 43. The filament heating circuitry 35 may adopt either a variable resistance type or a high frequency heating type.

The tube voltage detector 37 is connected between the anode side high voltage cable and the cathode side high voltage cable. The tube voltage detector 37 detects, as a tube voltage, a high voltage applied between the cathode 131 and the anode 133. The detected tube voltage value data is supplied to the tube voltage control circuitry 41.

The tube current detector 39 is connected to the anode side cable. The tube current detector 39 detects, as a tube current, a current that flows to the anode side cable due to the flow of thermoelectrons from the cathode 131 to the anode 133. The detected tube current value data is supplied to the tube current control circuitry 43.

The tube voltage control circuitry 41 controls the high voltage generation circuitry 33 based on a comparison between the tube voltage detection value and a set tube voltage value. Specifically, the tube voltage control circuitry 41 compares the tube voltage detection value with the set tube voltage value, and performs feedback control to the high voltage generation circuitry 33 so that the tube voltage detection value converges to the set tube voltage value. The set tube voltage value data is supplied from the gantry control circuitry 29.

The tube current control circuitry 43 controls the filament heating circuitry 35 based on a comparison between the tube current detection value and a set tube current value. Specifically, the tube current control circuitry 43 compares the tube current detection value with the set tube current value, and performs feedback control to the filament heating circuitry 35 so that the tube current detection value converges to the set tube current value. The set tube current value data is supplied from the gantry control circuitry 29.

The bias voltage generation circuitry 45 generates a bias voltage to be applied to the first grid electrode 137-1 in accordance with control by the bias voltage control circuitry 47. Similarly, the bias voltage generation circuitry 45 generates a bias voltage to be applied to the second grid electrode 137-2 in accordance with control by the bias voltage control circuitry 47.

The bias voltage control circuitry 47 controls the bias voltage generation circuitry 45 to selectively regulate the focus size corresponding to the first cathode 131-1 and the focus size corresponding to the second cathode 131-2. Specifically, the bias voltage control circuitry 47 stores in a memory, etc., a plurality of bias voltage values respectively corresponding to a plurality of predetermined focus sizes for the first cathode 131-1, and a plurality of bias voltage values respectively corresponding to a plurality of predetermined focus sizes for the second cathode 131-2. In the case where focus size information is supplied from the gantry control circuitry 29, the bias voltage control circuitry 47 reads from the memory, etc., a bias voltage value corresponding to a focus size of the cathode 131 (i.e., the first cathode 131-1 or the second cathode 131-2) indicated by the focus size information, and applies a voltage corresponding to the read bias voltage value to the grid electrode 137.

The filament heating circuitry 35 is switchably connected to the first cathode 131-1 or the second cathode 131-2 via a switch 49. The switch 49 selectively connects the filament heating circuitry 35 to the first cathode 131-1 or the second cathode 131-2 in accordance with control by the gantry control circuitry 29. Specifically, in the case where the focus size information is supplied from the gantry control circuitry 29, the switch 49 connects the filament heating circuitry 35 to the cathode 131 corresponding to the focus size information.

As shown in FIG. 1, the rotation frame 11 rotates about a center axis Z at a predetermined angular velocity upon receiving power from a rotation motor 21. The rotation motor 21 may be any motor such as a direct drive motor, a servo motor, etc. The rotation motor 21 is housed, for example, in the gantry 10. The rotation motor 21 generates power to rotate the rotation frame 11 upon receiving a driving signal from the gantry control circuitry 29.

An FOV is set in the bore of the rotation frame 11. A top plate supported by a bed 23 is inserted into the bore of the rotation frame 11. The subject P is placed on the top plate. The bed 23 movably supports the top plate. A bed motor 25 is housed in the bed 23. The bed motor 25 generates power to move the top plate in the longitudinal direction, the vertical direction, and the widthwise direction upon receiving a driving signal from the gantry control circuitry 29. The bed 23 regulates the top plate so that an imaging target portion of the subject P is included within the FOV.

The X-ray detector 15 detects X-rays generated by the X-ray tube 13. Specifically, the X-ray detector 15 includes a plurality of X-ray detection elements arranged on a two-dimensional curved surface. The X-ray detection elements each include a scintillator and a photoelectric conversion element. The scintillator is formed of a material that converts X-rays into light. The scintillator converts the applied X-rays into photons of a number corresponding to the intensity of the applied X-rays. The photoelectric conversion element is a circuit element that amplifies light received from the scintillator and converts the received light into an electrical signal. For example, a photomultiplier tube or a photodiode, etc. is applied as the photoelectric conversion element. The X-ray detection elements may adopt an indirect detection type detection element that converts X-rays into light and then detects the light, or a direct conversion type detection element that directly converts X-rays into an electrical signal.

The X-ray detector 15 is connected to data acquisition circuitry 19. In accordance with the instruction from the gantry control circuitry 29, the data acquisition circuitry 19 reads from the X-ray detector 15 an electrical signal corresponding to the intensity of X-rays detected by the X-ray detector 15, and acquires raw data having a digital value corresponding to the dose of X-rays during a view period. The data acquisition circuitry 19 acquires electrical signals from the plurality of X-ray detection elements and bundles the acquired electrical signals in bundle units in accordance with a resolution mode of the X-ray detector 15. The data acquisition circuitry 19 is implemented by, for example, an Application Specific Integrated Circuit (ASIC) on which a circuit element that is capable of generating raw data is mounted.

FIG. 5 is a schematic plane view showing an array of X-ray detection elements 151 included in the X-ray detector 15 according to the present embodiment. As shown in FIG. 5, a plurality of X-ray detection elements 151 are arranged two-dimensionally in the channel direction and the row direction. The row direction is defined as a direction along a rotation axis Z, and the channel direction is defined as a rotational direction about the rotation axis Z of the X-ray detector 15. The X-ray detection elements 151 according to the present embodiment are high resolution X-ray detection elements.

The X-ray detector 15 according to the present embodiment is capable of changing the resolution regarding the channel direction and the row direction. The resolution mode includes a super high resolution mode, a high resolution mode, and a normal resolution mode. The super high resolution mode, the high resolution mode, and the normal resolution mode are electrically switchable by the gantry control circuitry 29, etc.

The super high resolution mode is a mode where the pitch of reading channels 151SHR in the channel direction and the row direction is equal to the pitch of the X-ray detection elements 151. In the super high resolution mode, the data acquisition circuitry 19 reads an electrical signal from a X-ray detection element 151 which forms a reading channel 152SHR. The read electrical signal is processed as an electrical signal of one reading channel 152SHR.

Figure 6:
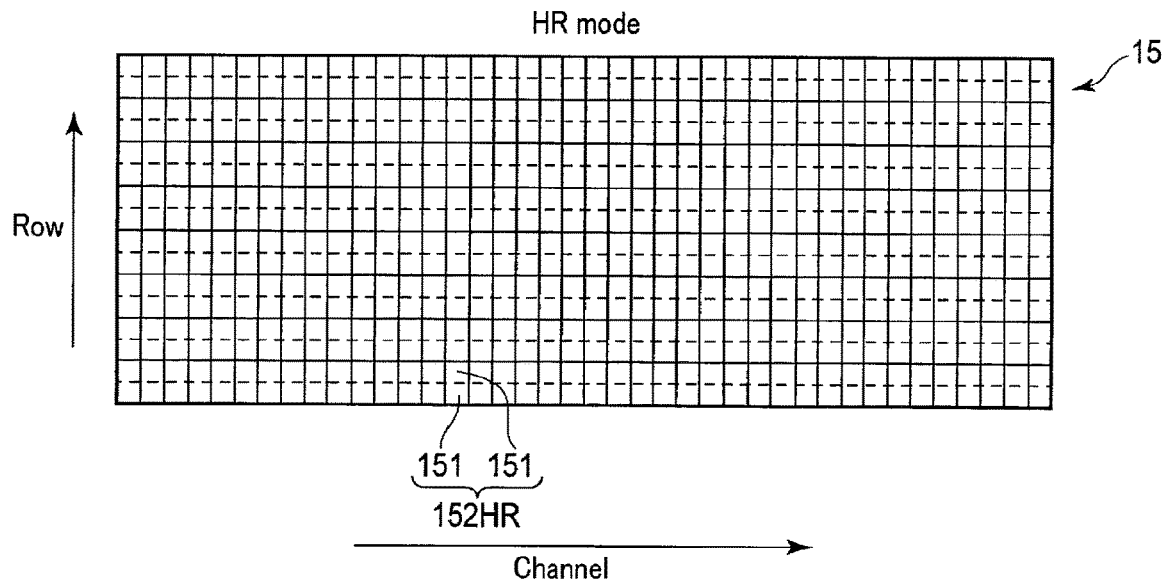
FIG. 6 is a schematic plane view of the reading channels of the X-ray detector in a high resolution mode.

FIG. 6 is a schematic plane view showing an arrangement of X-ray detection elements 151 of the X-ray detector 15 in the high resolution mode. As shown in FIG. 6, the high resolution mode is a mode where the pitch of reading channels 151HR in the channel direction is equal to the pitch of the X-ray detection elements 151, and the pitch of reading channels 151HR in the row direction is greater than the pitch of the X-ray detection elements 151. For example, in the case where the pitch in the high resolution mode is one-fold of (equal to) the pitch in the super high resolution mode in the channel direction, and is twofold of the pitch in the super high resolution mode in the row direction, two X-ray detection elements 151 (2 (in the row direction)×1 (in the channel direction)) form a reading channel 152HR. The data acquisition circuitry 19 bundles (integrates) electrical signals from two X-ray detection elements 151 that form a reading channel 152HR. The read electrical signal is processed as an electrical signal of one reading channel 152SHR.

Figure 7:
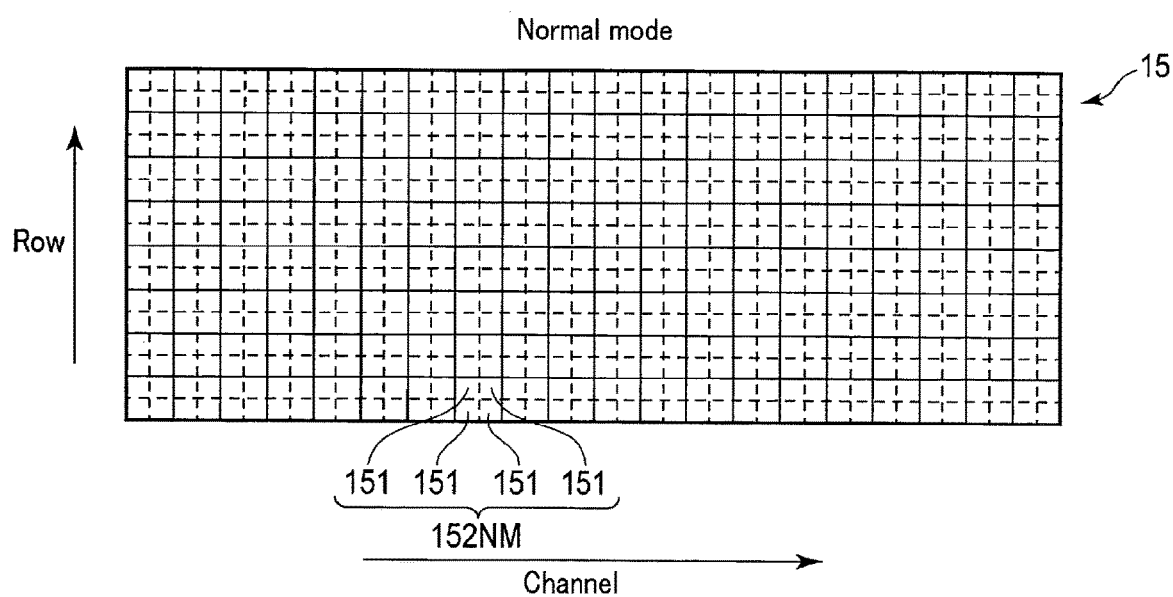
FIG. 7 is a schematic plane view of the reading channels of the X-ray detector in a normal resolution mode.

FIG. 7 is a schematic plane view showing an arrangement of X-ray detection elements 151 of the X-ray detector 15 in the normal resolution mode. As shown in FIG. 7, the normal resolution mode is a mode where the pitch of reading channels 151NM in the channel direction and the row direction is greater than the pitch of the X-ray detection elements 151. For example, in the case where the pitch in the normal resolution mode is twofold of the pitch in the super high resolution mode in the channel direction and the row direction, four X-ray detection elements 151 (2 (in the row direction)×2 (in the channel direction)) form a reading channel 152NM in the normal resolution mode. The data acquisition circuitry 19 combines and reads electrical signals from four X-ray detection elements 151 that form a reading channel 152NM. The combined electrical signal is processed as an electrical signal of one reading channel 152NM.

As shown in FIG. 1, the gantry control circuitry 29 synchronously controls the high voltage generator 17, the data acquisition circuitry 19, the rotation motor 21, and the bed motor 25, to perform X-ray CT imaging in accordance with imaging conditions obtained from the processing circuitry 101 of the console 100. The gantry control circuitry 29 includes a processor, such as a CPU (Central Processing Unit) and an MPU (Micro Processing Unit), and a memory, such as a ROM (Read Only Memory) and a RAM (Random Access Memory), as hardware resources. The gantry control circuitry 29 may be implemented by an ASIC or a Field Programmable Gate Array (FPGA), a CPLD (Complex Programmable Logic Device), or an SPLD (Simple Programmable Logic Device).

As shown in FIG. 1, the console 100 includes the processing circuitry 101, a display 103, an input interface 105, and a memory 107. Data communication is performed between the processing circuitry 101, the display 103, the input interface 105, and the memory 107 via a bus.

The processing circuitry 101 includes a processor such as a CPU, an MPU, or a GPU (Graphics Processing Unit), etc. and a memory such as a ROM or a RAM, etc. as hardware resources. The processing circuitry 101 executes various programs to implement a preprocessing function 111, a reconstruction function 113, an image processing function 115, and a system control function 123. The processing circuitry 101 executes a focus size determination program according to the present embodiment to implement a condition determination function 117, a focus size determination function 119, and a waiting time calculation function 121.

By the preprocessing function 111, the processing circuitry 101 performs preprocessing such as logarithmic conversion to raw data transmitted from the gantry 10. The preprocessed raw data is also referred to as projection data.

By the reconstruction function 113, the processing circuitry 101 generates a CT image representing a space distribution of CT values relating to the subject P based on the preprocessed raw data. The known image reconstruction algorithm such as an FBP (Filtered Back Projection) method or a successive approximation reconstruction method, may be adopted.

By the image processing function 115, the processing circuitry 101 performs various image processing to a CT image reconstructed by the reconstruction function 113. For example, the processing circuitry 101 performs three-dimensional image processing, such as volume rendering, surface volume rendering, image value projection processing, Multi-Planer Reconstruction (MPR) processing, Curved MPR (CPR) processing, etc. to the CT image to generate a display image.

By the condition determination function 117, the processing circuitry 101 determines a resolution mode, an application dose condition, and an X-ray exposure time for target CT imaging. The imaging condition determined by the condition determination function 117 is referred to as an input condition. The application dose condition includes at least one of a set dose value or information regarding a physique of the subject (hereinafter referred to as "physique information"). The set dose value is a set value of an application dose. The set dose value may be set by a parameter of the set dose value, or may be set by a combination of the set tube voltage value and the set tube current value. In the following description, it is assumed that the set dose value is set by a combination of the set tube voltage value and the set tube current value. The physique information may be a size of FOV, a body measurement value of the subject, such as abdominal circumference or abdominal thickness, etc., or classification information of a physique of the subject, such as ectomorph, endomorph, etc.

By the focus size determination function 119, the processing circuitry 101 determines a focus size for the target CT imaging based on the resolution mode, application dose condition, and physique information determined by the condition determination function 117. For example, the processing circuitry 101 determines the focus size applied to the target CT imaging among a plurality of focus sizes, based on the resolution mode, set dose value (the set tube current value and the set tube voltage value), and X-ray exposure time determined by the condition determination function 117 by using a time-tube current table as described below. The time-tube current table is stored in the memory 107. The processing circuitry 101 may determine the focus size without using the table.

By the waiting time calculation function 121, the processing circuitry 101 calculates a waiting time until CT imaging is initiated with the focus size determined by the focus size determination function 119. The waiting time is a time required for the X-ray tube 13 to be sufficiently cooled down.

By the system control function 123, the processing circuitry 101 integrally controls the X-ray computed tomography apparatus according to the present embodiment. Specifically, the processing circuitry 101 reads a control program stored in the memory 107, deploys the control program, and controls the respective units of the X-ray computed tomography apparatus in accordance with the deployed control program.

The preprocessing function 111, the reconstruction function 113, the image processing function 115, the condition determination function 117, the focus size determination function 119, the waiting time calculation function 121, and the system control function 123 may be implemented by the processing circuitry 101 on a certain substrate, or may be implemented by the processing circuitry 101 distributed over a plurality of substrates.

The display 103 displays various data, such as a setting window of a focus size, a CT image, etc. Specifically, the display 103 is connected to a display interface. The display interface converts data representing a display target to a video signal. The video signal is supplied to the display 103. The display 103 displays the video signal which represents the display target. For example, a CRT display, a liquid crystal display, an organic EL display, an LED display, a plasma display, or any other display known in this technical field may be adopted as the display 103.

The input interface 105 accepts various instructions from the user. Specifically, the input interface 105 is connected to an input device. The input device receives various instructions from the user. For example, a keyboard, a mouse, or switches etc. may be used as the input device. The input interface 105 supplies an output signal from the input device to the processing circuitry 101 via a bus.

The memory 107 is a storage device such as an HDD, an SSD, or an integrated circuit storage unit, etc., configured to store various kinds of information. The memory 107 may be a drive, etc. configured to read and write various kinds of information with respect to a portable storage medium such as a CD-ROM drive, a DVD drive, or a flash memory, etc. For example, the memory 107 stores a control program, etc. relating to CT imaging according to the present embodiment. The memory 107 also stores a time-tube current table 141 and a width-tube current table 143. The time-tube current table 141 is generated for respective combinations of the tube voltage value and an OLP (Overload Protection)

value. The time-tube current table defines the relationship between an allowable continuous X-ray exposure time and the tube current value (the time-tube current relationship) for respective focus sizes. The time-tube current relationship corresponds to a short time rating. The width-tube current table 143 defines the relationship between the tube current value and the width (hereinafter referred to as "tube current-width correspondence") for respective focus sizes.

Figure 8:
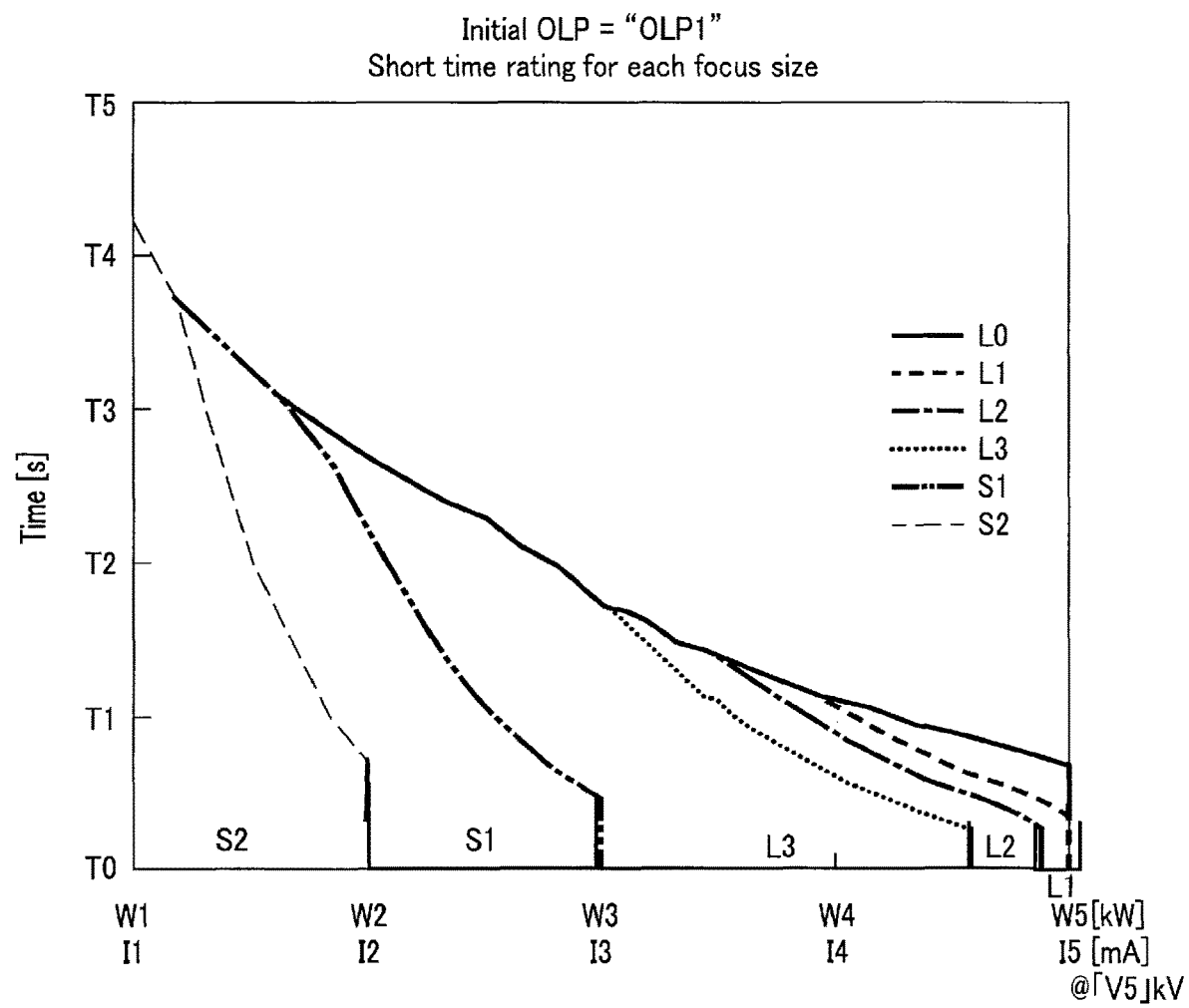
FIG. 8 is a schematic view of the relationship between the allowable continuous X-ray exposure time and the tube current (time-tube current relationship) for respective focus sizes indicated by a time-tube current table stored in a memory shown in FIG. 1.

FIG. 8 is a schematic view of the relationship between the allowable continuous X-ray exposure time and the tube current value (the time-tube current relationship) for respective focus sizes indicated by the time-tube current table. In FIG. 8, the ordinate represents an allowable continuous X-ray exposure time [s], and the abscissa represents a set power value [kW] and a set tube current value [mA]. Specifically, FIG. 8 illustrates the relationship between the allowable continuous X-ray exposure time and the tube current value for respective focus sizes where the OLP value is "OLP1" % and the tube voltage value is "V5" kV. The OLP value represents a degree of load currently applied to the X-ray tube 13. For example, the OLP value is defined by a numeric value representing the current loading condition of the X-ray tube 13 by percentage when the saturation state of a load such as heat, etc. accumulated in the X-ray tube 13 is 100%. The short time rating represents the continuous X-ray exposure time until the load reaches the saturation state in the case where X-ray exposure is performed under a given focus size, OLP value, set tube voltage value, and set tube current value.

As stated above, the parameters of focus size are defined by the length LL and the width WL. The length LL corresponds to the length of a filament included in the cathode 131, and is classified into a long length (L) corresponding to the cathode 131-1, and a short length (S) corresponding to the cathode 131-2. The width WL is classified into L0, L1, L2, and L3 in an order from greater to smaller for the long cathode 131-1, and is classified into S0, S1, and S2 in an order from greater to smaller for the short cathode 131-2.

The focus size is represented as an area defined by width [mm]×length [mm]. It is not necessarily the case where a focus size Ln of the long cathode 131-1 is designed to be greater than a focus size Sn of the short cathode. The width and the length of each focus size may be a discretionarily designed value. For example, the width of S1 may be substantially the same as the width of L3, and the width of S1 may be greater than the width of L3. Accordingly, in the present embodiment, the width of the long focus size Ln does not necessarily have to be greater than that of the short focus size Sn. It is possible to design the width of the short focus size to be greater than that of the long focus size. Thus, it is possible to realize CT imaging in which the in-plane resolution is prioritized, but not in the resolution in the row direction, for example, in the case where the focus size L3 is selected.

In the aforementioned explanation, three focus sizes are prepared for the long cathode 131-1 and the short cathode 131-2. However, the number of focus sizes is not limited thereto in the present embodiment. That is, the number of focus sizes may be different between the long cathode 131-1 and the short cathode 131-2. Two focus sizes, or four or more focus sizes may be prepared for each of the long cathode 131-1 and the short cathode 131-2.

Figure 9:
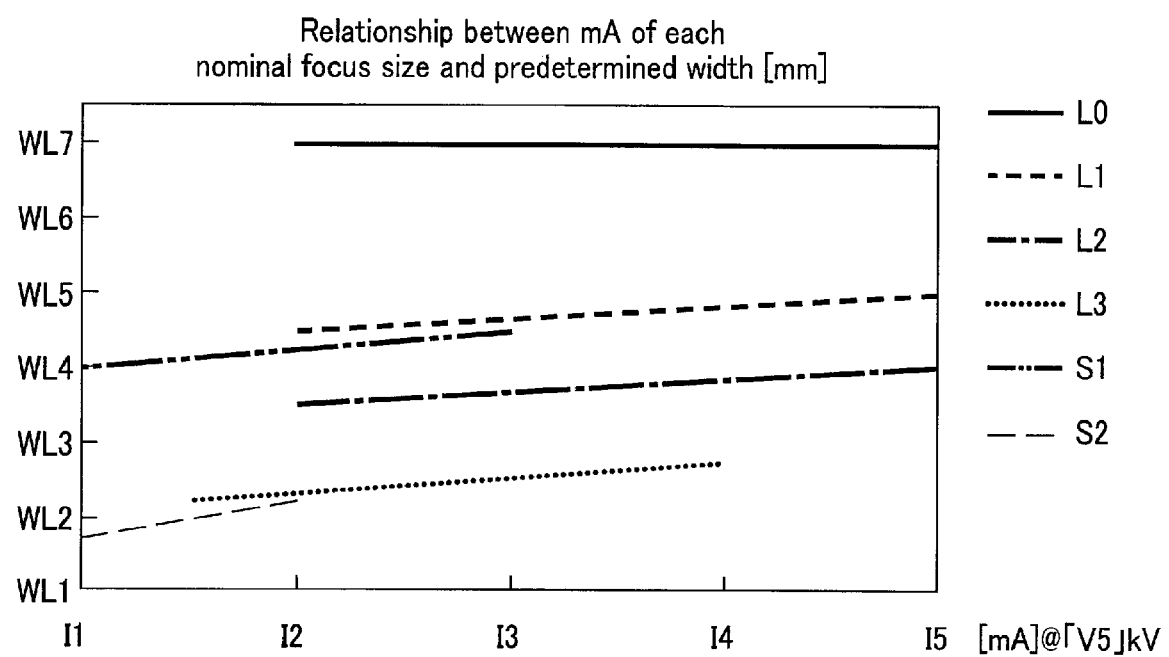
FIG. 9 is a schematic view of the relationship between the tube current and the width (tube current-width correspondence) for respective focus sizes indicated by a width-tube current table stored in a memory shown in FIG. 1.

FIG. 9 is a schematic view of the relationship between the tube current and the width (tube current-width correspondence) for respective focus sizes indicated by a width-tube current table. In FIG. 9, the ordinate represents a predetermined width [mm], and the abscissa represents a set tube current value [mA]. As shown in FIG. 9, the width of the focus varies in accordance with the variation of the set tube current value in the case where the set tube current value changes under a fixed nominal focus size and a fixed set tube voltage value (e.g., "V5" kV).

In the following description, an operation example of the X-ray computed tomography apparatus according to the present embodiment will be explained.

Figure 10:
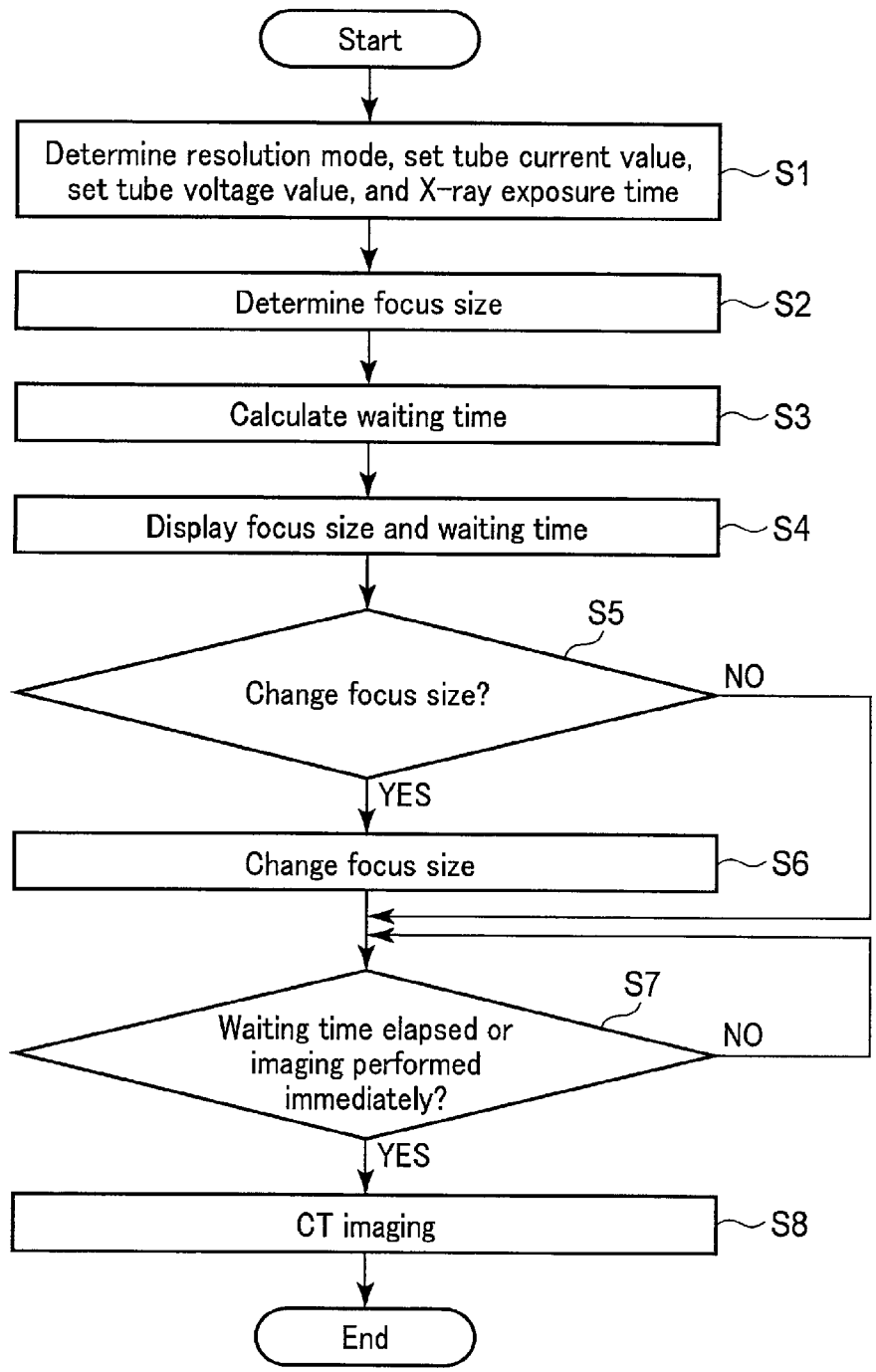
FIG. 10 is a flowchart of the typical processing of the X-ray computed tomography apparatus according to the present embodiment.

FIG. 10 is a flowchart of the typical processing of the X-ray computed tomography apparatus according to the present embodiment. As shown in FIG. 10, the processing circuitry 101 reads and executes the control program stored in the memory 107 and initiates a series of processing shown in FIG. 10, upon receiving a setting instruction, etc. for a scanning plan that includes an imaging condition, etc.

As shown in FIG. 10, the processing circuitry 101 executes the condition determination function 117 (step S1). In step S1, the processing circuitry 101 determines input conditions such as a resolution mode, a set tube current value, a set tube voltage value, and an X-ray exposure time, etc. related to CT imaging for which the scanning plan is set. The resolution mode, the set tube current value, the set tube voltage value, and the X-ray exposure time may be selected at the user's discretion through the input interface 105, or may be automatically determined in accordance with an other input condition or imaging condition based on a predetermined rule.

After step S1, the processing circuitry 101 executes the focus size determination function 119 (step S2). In step S2, the processing circuitry 101 determines a focus size by applying the resolution mode, set tube current value, set tube voltage value, and X-ray exposure time determined in step S1 to the time-tube current table 141.

The resolution mode, set tube current value, set tube voltage value, and X-ray exposure time may be determined in any order. Typically, the processing circuitry 101 determines the resolution mode, the set tube current value, the set tube voltage value, the X-ray exposure time, and the focus size, in the order given. Based on the determined resolution mode, a settable set tube voltage value, set tube current value, and X-ray exposure time are narrowed down. Specifically, when determining the focus size, the processing circuitry 101 determines the imaging conditions in accordance with a table (hereinafter referred to as "imaging condition table") in which imaging conditions including a set tube voltage value, a set tube current value, and an X-ray exposure time, etc. settable based on the resolution mode, are defined.

FIG. 11 shows an example of an imaging condition table. The selectable resolution modes include a super high resolution (SHR), a high resolution (HR), and a normal resolution. As an example, in the super high resolution mode, the pitch of reading channels in the row direction is "nSL" mm, and the number of reading channels in the channel direction is m CH. The pitch number nSL and the reading channel number m CH may be any value. In the high resolution mode, the reading channel pitch in the row direction is "2mSL" mm, which is twofold of the pitch in the super high resolution mode, and the reading channel number in the channel direction is m CH, which is equal to the number in the super high resolution mode. In the normal resolution mode, the reading channel pitch in the row direction is "2mSL" mm, which is twofold of the pitch in the super high resolution mode, and the reading channel number in the channel direction is "m/2" CH, which is half of the number in the super high resolution mode. The resolution mode is discretionarily selected by the user through the input interface 105, for example.

As shown in FIG. 11, in the super high resolution mode, the reading channel pitch in the row direction is half of that in the high resolution mode. That is, the super high resolution mode is selected in the case where the resolution in the row direction (i.e., the body axis direction of the subject P) is prioritized. Accordingly, if the super high resolution mode is selected, the focus size having a shorter length is preferred.

In the high resolution mode, the reading channel pitch in the row direction is twofold in comparison with the super high resolution mode. In addition, the reading channel number in the channel direction is twofold in comparison with the normal resolution mode. That is, the high resolution mode is selected in the case where the resolution in the row direction is not prioritized, but the resolution of a slice plane is prioritized. Accordingly, if the high resolution mode is selected, the focus size having a smaller width is preferred.

In the normal resolution mode, the pitch in the row direction is the same as that in the high resolution mode, and the reading channel number in the channel direction is half in comparison with the super high resolution mode. That is, the normal resolution mode is selected in the case where the in-plane resolution is not prioritized, but the throughput and the S/N ratio are prioritized. Accordingly, if the normal resolution mode is selected, the focus size having a longer length and a longer width is preferred.

As shown in FIG. 11, the size of a part (i.e., FOV), a set tube voltage value [kVp], a set tube current value (maximum mA) and an X-ray exposure time are automatically determined in accordance with a predetermined rule, or determined by the user through the input interface 105. For example, the FOV, set tube voltage value, set tube current value, and X-ray exposure time are determined in the order given. The FOV is determined, for example, among a small size S, a medium size M, and a large size L.

As shown in FIG. 11, the allowable range of the set tube voltage value is defined for each resolution mode. Specifically, in the super high resolution mode, the set tube voltage value is limited from "V5" kV to "V10" kV. In the high resolution mode, the allowable range of the set tube voltage value is different depending on the FOV. Specifically, if the FOV is an S size, the set tube voltage value is limited from "V4" kV to "V10" kV, and if the FOV is an M size or an L size, the set tube voltage value is limited from "V5" kV to "V10" kV. In the normal resolution mode, the set tube voltage value is limited from "V3" kV to "V10" kV. As the suffix of V increases, the indicated tube voltage value increases.

As shown in FIG. 11, focus size candidates are defined for each resolution mode. Specifically, the focus sizes S2, S1, L3 and L2 are defined as focus size candidates for the super high resolution mode. The focus sizes S2, S1, L3, L2, and L1 are defined as focus size candidates for the high resolution mode. The focus sizes S2, S1, L3, L2, L1 and L0 are defined as focus size candidates for the normal resolution mode.

The X-ray exposure time can typically be set to be any value regardless of the resolution mode. However, the allowable range of the X-ray exposure time may be limited in accordance with the resolution mode, etc.

The method for determining a focus size will be explained in detail with reference to three examples as below.

Example 1

In Example 1, the super high resolution mode is selected, the set tube voltage value is "V5" kV, the X-ray exposure time is "Th1" seconds, and imaging is performed with a focus size which is as small as possible. The OLP value in focus size determination processing is "OLP1" %.

Figure 13:
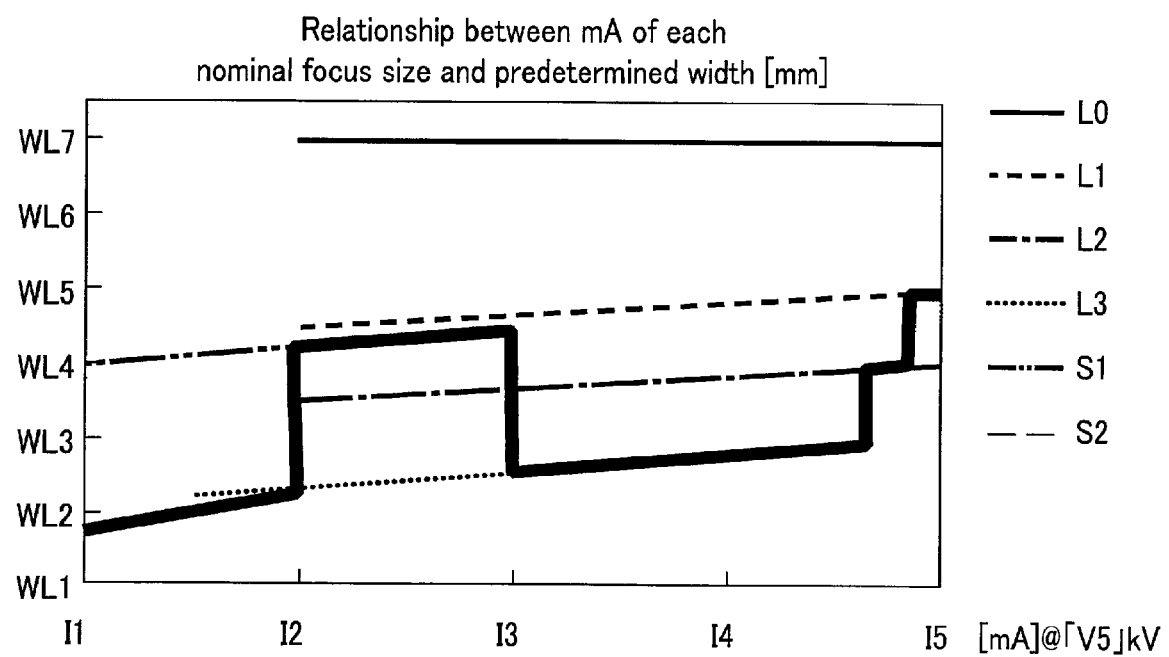
FIG. 13 is a graph showing the tube current-width correspondence under the conditions of example 1.

FIG. 12 shows the time-tube current relationship under the condition of Example 1, and FIG. 13 shows the tube current-width correspondence under the condition of Example 1. As shown in FIG. 12, the focus size candidates that comply with the condition are indicated by bold lines. That is, since the super high resolution mode is selected, the smallest possible focus size is selected. Since the X-ray exposure time is "Th1" seconds which is relatively short, a focus size having the allowable continuous X-ray exposure time of longer than "Th1" seconds is selected as a candidate. That is, a focus size having the allowable continuous X-ray exposure time of shorter than "Th1" seconds is eliminated from the focus size candidates. For example, if the set tube current value is determined to be a value between I2 and I3, the focus size is determined as S1.

Example 2

In Example 2, the super high resolution mode is selected, the set tube voltage value is "V5" kV, the X-ray exposure time is "Th2" seconds, and imaging is performed by maintaining the in-plane resolution level to the greatest extent possible. The OLP value in focus size determination processing is "OLP1" %.

Figure 14:
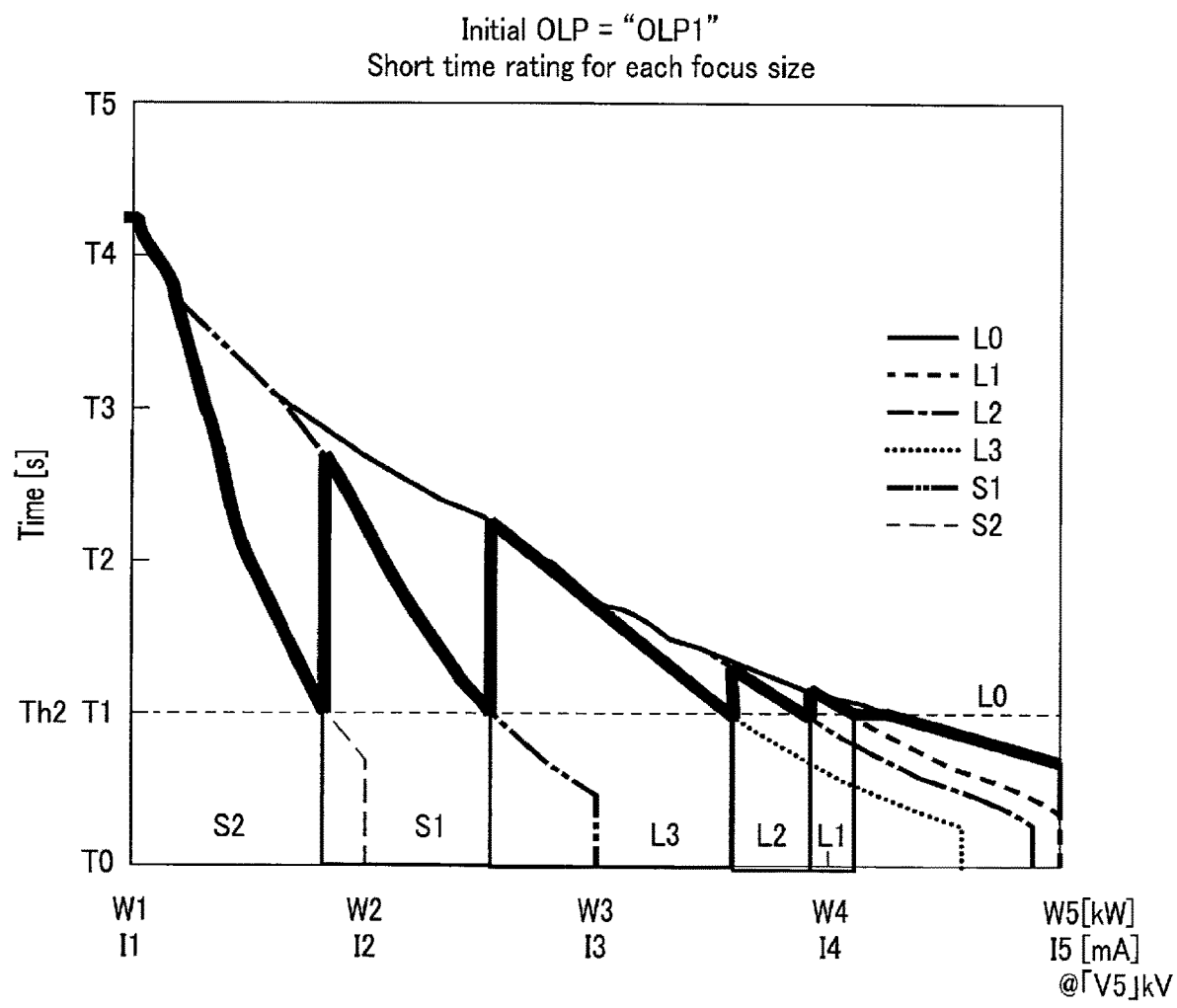
FIG. 14 is a graph showing the time-tube current relationship under conditions of example 2.
Figure 15:
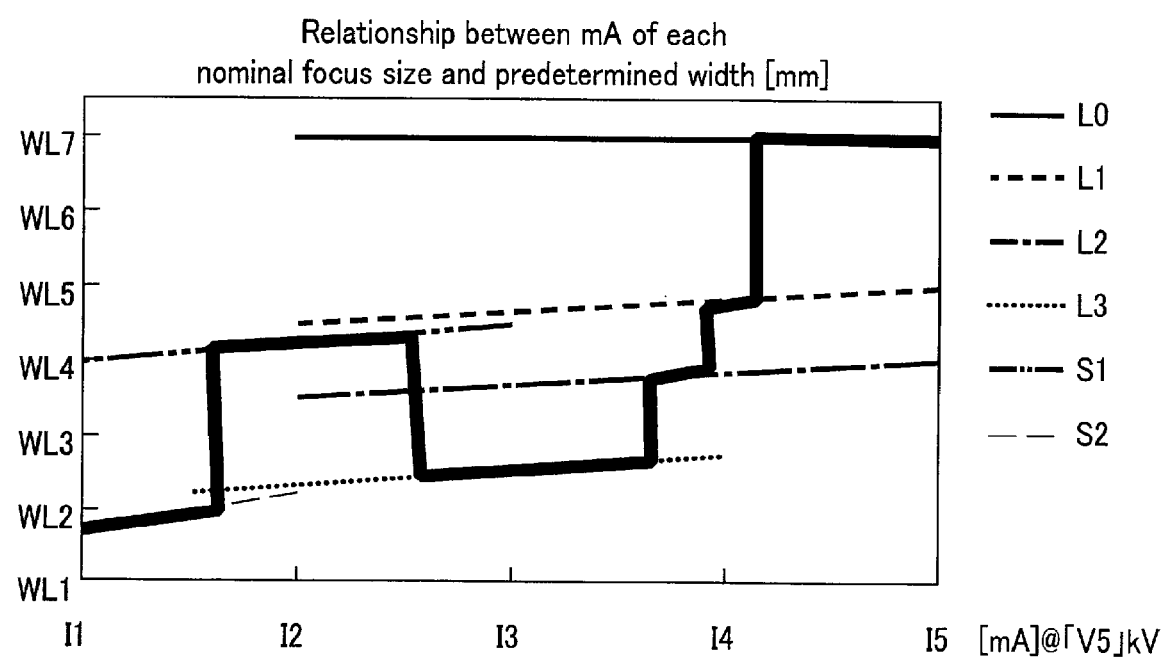
FIG. 15 is a graph showing the tube current-width correspondence under the conditions of example 2.

FIG. 14 shows the time-tube current relationship under the condition of Example 2, and FIG. 15 shows the tube current-width correspondence under the condition of Example 2. As shown in FIG. 14, the focus size candidates that comply with the condition are indicated by bold lines. That is, since the super high resolution mode is selected, the focus size as small as possible is selected. However, under the condition of maintaining the in-plane resolution level to the greatest extent possible, a focus size of a smaller width is selected among the focus sizes that comply with the condition. Since the X-ray exposure time is "Th2" seconds which is relatively long, a focus size having the allowable continuous X-ray exposure time of longer than "Th2" seconds is selected as a candidate. That is, a focus size having the allowable continuous X-ray exposure time of shorter than "Th2" seconds is eliminated from the focus size candidates. For example, in the case where the set tube current value is determined as I3, the focus size is determined as L3.

Example 3

In Example 3, imaging is performed by maintaining the in-plane resolution level for a maximum time duration and with a maximum value under the condition where the high resolution mode is selected, the set tube voltage value is "V5" kV, and the X-ray exposure time is set to be as long as possible. The OLP value in focus size determination processing is "OLP1" %.

Figure 16:
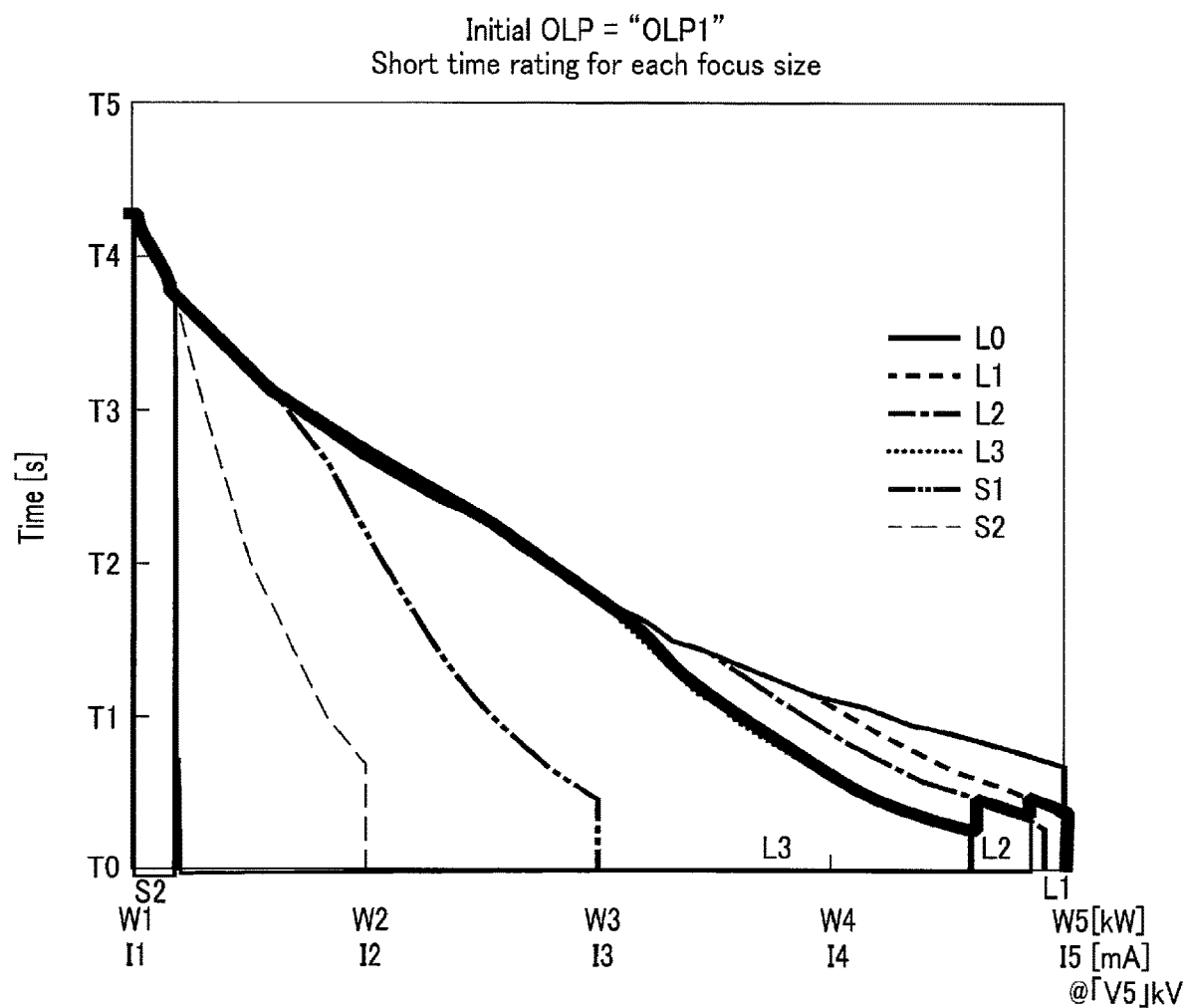
FIG. 16 is a graph showing the time-tube current relationship under conditions of example 3.
Figure 17:
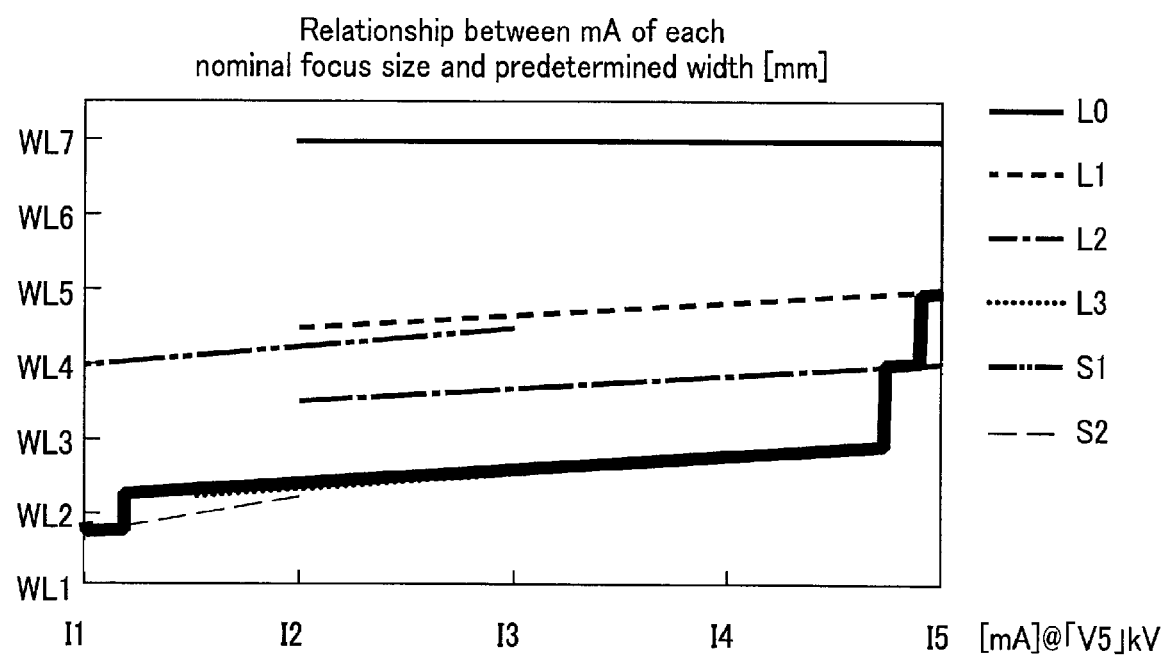
FIG. 17 is a graph showing the tube current-width correspondence under the conditions of example 3.

FIG. 16 shows the time-tube current relationship under the condition of Example 3, and FIG. 17 shows the tube current-width correspondence under the condition of Example 3. As shown in FIG. 16, the focus size candidates that comply with the condition are indicated by bold lines. That is, since the high resolution mode is selected, the focus size having a width as small as possible is selected. Since the condition shows that the X-ray exposure time is as long as possible, a focus size having the longest allowable continuous X-ray exposure time is selected as a candidate. For example, in the case where the set tube current value is determined as I3, the focus size is determined as L3.

According to Examples 1, 2, and 3, a focus size optimal to the input conditions determined in step S1 can be determined.

After step S2, the processing circuitry 101 executes the waiting time calculation function 121 (step S3). In step S3, the processing circuitry 101 calculates a waiting time required to perform CT imaging with the focus size determined in step S2.

The waiting time can be calculated by applying the determined focus size to the aforementioned short time rating. For example, the processing circuitry 101 calculates an allowable continuous X-ray exposure time by applying the determined focus size to the short time rating, and compares the X-ray exposure time and the calculated allowable continuous X-ray exposure time. If the X-ray exposure time is shorter than the allowable continuous X-ray exposure time, the processing circuitry 101 determines that the waiting time is zero. If the X-ray exposure time is longer than the allowable continuous X-ray exposure time, the processing circuitry 101 determines that the waiting time is not zero. In this case, the processing circuitry 101 calculates a time required until the allowable continuous X-ray exposure time becomes equal to the X-ray exposure time as a waiting time. For example, the processing circuitry 101 calculates an increase or decrease amount of OLP value to increase the allowable continuous X-ray exposure time by a time corresponding to the difference between the allowable continuous X-ray exposure time and the X-ray exposure time, and multiplies the increase or decrease amount of OLP value by a changing rate of OLP value over time to obtain the waiting time. Specifically, in the case where the time required until the allowable continuous X-ray exposure time becomes equal to the X-ray exposure time is 5 seconds, the increase or decrease amount of OLP value corresponding to 5 seconds is 20%, the changing rate of OLP value over time is 5%/s, and the waiting time is 20/5=4 s.

After step S3, the processing circuitry 101 directs the display 103 to perform display processing (step S4). In step S4, the display 103 displays the focus size determined in step S2 and the waiting time calculated in step S3. Since the waiting time is displayed, the user can determine whether or not CT imaging can be immediately performed with the determined focus size. In step S4, the display 103 may display the determined resolution mode, the set tube voltage value and the set tube current value determined in step S1 together with the focus size.

After step S4, the processing circuitry 101 determines whether or not an instruction for changing the focus size is input (step S5). For example, in the case where CT imaging is performed for an emergency patient P, CT imaging should be performed immediately. In this case, the user performs an instruction for changing the focus size through the input interface 105. On the other hand, in the case where CT imaging is performed for a non-emergency patient P, i.e., not for the emergency patient P, and can be performed after a waiting time, the user may not perform an instruction for changing the focus size.

After step S5, if the instruction for changing the focus size is performed (step S5: Yes), the processing circuitry 101 executes the focus size determination function 119 again (step S6). In step S6, the processing circuitry 101 changes the focus size. Specifically, a focus size with which CT imaging can be performed immediately and in which any one of input conditions determined in step S1 is disregarded is determined. The state where CT imaging can be performed immediately indicates that the waiting time is zero.

In the case where a waiting time is required until the X-ray tube 13 is cooled down to adopt the focus size determined in step S2, the processing circuitry 101 searches for a focus size with which CT imaging can be performed immediately by changing a value of an input condition that has a low priority while a value of an input condition having a high priority is being fixed. Any input conditions among the resolution mode, the set tube current value, the set tube voltage value, and the X-ray exposure time may be disregarded.

For example, in the case where a waiting time is required until the X-ray tube 13 is cooled down (i.e., the waiting time is not zero), it is assumed that the resolution mode, the set tube current value, and the set tube voltage value are fixed, and the X-ray exposure time is reduced. In this case, it is possible to change the focus size to a focus size that requires less waiting time.

For another example, in the case where a waiting time is required until the X-ray tube 13 is cooled down, it is assumed that the set tube current value, the set tube voltage value, and the X-ray exposure time are fixed, and the resolution mode is changed to a lower resolution mode. For example, by changing the resolution mode to a lower resolution mode, a focus size having a larger length and width is selectable, and accordingly, a focus size that requires less waiting time can be adopted.

For another example, there may be a case where the resolution in the row direction of the X-ray detector 15 is disregarded. By changing the resolution mode to the resolution mode in which the resolution in the row direction is lower, the length of the focus size is widened. Accordingly, the degradation of the anode 133 can be reduced, and the continuous X-ray exposure time can be increased. In addition, the set tube current value can be increased.

If an instruction for changing a focus size is not performed in step S4 (step S5: No), or step S6 is executed, the processing circuitry 101 determines whether or not a waiting time has elapsed, or whether or not imaging with the determined focus size can be performed immediately (step S7).

In step S7, it is determined that a waiting time has not elapsed (step S7: No), the processing circuitry 101 waits until the waiting time has elapsed.

If it is determined that a waiting time has elapsed, or that imaging with the determined focus size can be performed immediately in step S7 (step S7: Yes), the processing circuitry 101 directs the gantry control circuitry 29 to perform CT imaging (step S8). In step S8, the gantry control circuitry 29 controls the high voltage generator 17, the data acquisition circuitry 19, the rotation motor 21, and the bed motor 25, to perform CT imaging with the determined resolution mode, set tube current value, set tube voltage value, X-ray exposure time, and focus size. By this processing, CT imaging with the focus size suitable for the input conditions determined in step S1 can be performed.

The operation example of the X-ray computed tomography imaging apparatus according to the present embodiment is completed with the above explanations.

Modification

In the above explanations, the processing circuitry 101 determines among predetermined multiple focus sizes the focus size that satisfies the input conditions that are determined by the condition determination function 117, by using the time-tube current table 141 and/or the width-tube current table 143. However, the present embodiment is not limited thereto. In the following description, another method for determining a focus size will be explained.

According to another determination method, the processing circuitry 101 determines a given focus size based on input conditions such as determined resolution mode, application dose condition, and X-ray exposure time, etc. The "given focus size" does not indicate a particular focus size among a predetermined plurality of focus sizes, but indicates a combination of a width and a length of a focus determined in accordance with an algorithm described below. Accordingly, the processing circuitry 101 can determine a focus size truly optimal to the input conditions regardless of a predetermined focus size. The gantry control circuitry 29 controls the high voltage generator 17 to form a focus having the determined width and length, and performs CT imaging. By this processing, CT imaging with the focus size optimal to the input conditions can be performed.

An example of a determination algorithm for a width and a length of a focus will be explained below. The processing circuitry 101 determines a width and a length of a focus size optimal to the determined input conditions such as a resolution mode, an application dose condition (for example, a set tube current value and a set tube voltage value), and an X-ray exposure time, etc.

FIG. 18 is a schematic diagram of procedures of a determination algorithm for a width and a length of a focus according to a modification. Similar to FIG. 8, FIG. 18 is a graph under the conditions where the OLP value is "OLP1"%, and the set tube voltage value is "V5" kV. The ordinate represents an allowable continuous X-ray exposure time [s], and the abscissa represents a set tube current value [mA]. The OLP value used for preparing a graph may be an actual OLP value when using the determination algorithm, or any predetermined OLP value.

As shown in FIG. 18, the processing circuitry 101 first plots a point Pt corresponding to an ordered pair of the determined set tube current value It and X-ray exposure time Tt. The set tube current value It and the X-ray exposure time Tt are initially determined in accordance with the physique information of the subject. For example, the processing circuitry 101 determines the set tube current value It and the X-ray exposure time Tt by referring to a table in which a set tube current value and an X-ray exposure time are associated with each other for each physique information. The processing circuitry 101 may determine the set tube current value It and the X-ray exposure time Tt in accordance with a tube current value and an X-ray exposure time input by the user through the input interface 105.

The processing circuitry 101 draws a time-tube current curve C0 relating to a particular focus size. The time-tube current curve is a curve on a graph in which the ordinate represents the allowable continuous X-ray exposure time, and the abscissa represents the set tube current value. The time-tube current curve C0 indicates an upper limit of a set tube current value and an allowable continuous X-ray exposure time with which CT imaging can be performed with the particular focus size. A particular focus size may have any width and length. For example, it is assumed that a particular focus size is an L0 size which is relatively large in the length, as shown in FIG. 18.

Next, the processing circuitry 101 modifies the time-tube current curve so that the time-tube current curve C0 intersects the point Pt, based on the resolution mode. For example, in the case where the user instructs performing CT imaging in the high resolution mode through the input interface 105, the processing circuitry 101 draws a time-tube current curve C1 regarding a focus size having a length suitable for the high resolution mode on the graph, based on the time-tube current curve C0 regarding the particular focus size. For example, if the time-tube current curve C0 is a curve corresponding to the focus size L, a curve corresponding to the focus size M0 is drawn as the time-tube current curve C1. The length of the focus size M0 is smaller than that of size L, and greater than that of size S. The width of the focus size M0 is the maximum settable value. For example, if a slice of a higher resolution is desired, in other words when a CT image of a thinner slice is desired, a focus size is changed to that having a short length.

If the time-tube current curve C1 intersects the point Pt, the length and the width corresponding to the curve C1 are determined as the length and the width of the focus of target CT imaging. If the curve C1 does not intersect the point Pt, the curve C1 is modified by changing the width of the focus size so as to intersect the point Pt. For example, in the case where the width of the focus size corresponding to the curve C1 is temporarily set to be maximum, the processing circuitry 101 modifies the curve C1 so that the width is reduced by a predetermined step width. The step width may be set by the user discretionarily through the input interface 105. If the width of the focus size corresponding to the curve C1 is temporarily set to be minimum, the processing circuitry 101 modifies the curve C1 so that the width is increased by a predetermined step width. If the width of the focus size corresponding to the curve C1 is temporarily set to be a value other than a maximum or minimum value, the processing circuitry 101 modifies the curve C1 so that the width is decreased or increased by a predetermined step width.

If the time-tube current curve Ct intersects the point Pt, the processing circuitry 101 determines the length and the width corresponding to the curve Ct to be the length and the width of the focus of a target CT imaging.

Based on the aforementioned algorithm, the focus size having the length and the width suitable for the input conditions such as the resolution mode, the application dose condition, and X-ray exposure time, etc. can be determined other than the prepared focus sizes.

As described above, according to the present embodiment, in the X-ray computed tomography apparatus which is capable of changing the resolution mode of the X-ray detector 15, the focus size for a designated resolution mode is determined in consideration of the resolution mode, namely, the pitch of reading channels in the channel direction and the row direction. In addition, according to the present embodiment, the degree of freedom to choose a focus size for a resolution mode is relatively high since a plurality of focus sizes which have a different combination of a length and a width are prepared respectively for a long focus and a short focus. Accordingly, an optimal focus size for a designated resolution mode can be determined.

Therefore, according to the present embodiment, a focus size suitable for imaging conditions can be determined.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography imaging apparatus comprising:
   an X-ray tube configured to generate X-rays;
   an X-ray detector comprising a plurality of X-ray detection elements configured to detect X-rays;
   an acquisition circuitry configured to acquire electrical signals from the plurality of X-ray detection elements and bundles the electrical signals in bundle units according to a resolution mode of the X-ray detector;
   a high voltage generator configured to control a dose and a focus size of the X-ray tube; and
   processing circuitry configured to determine a resolution mode, an application dose condition, and an X-ray exposure time for target CT imaging, and determine a focus size for the target CT imaging based on the determined resolution mode, application dose condition, and X-ray exposure time.

2. An X-ray computed tomography imaging apparatus according to claim 1, further comprising:
   a memory configured to store a table which indicates a relationship between an allowable continuous X-ray exposure time and a tube current value for each of a plurality of focus sizes that are associated with respective combinations of a tube voltage value and an OLP value,
   wherein the processing circuitry configured to determine the focus size for the target CT imaging among the plurality of focus sizes, based on the determined resolution mode, application dose condition, and X-ray exposure time by using the table.

3. An X-ray computed tomography imaging apparatus according to claim 1, further comprising:
   a display,
   wherein the processing circuitry calculates a waiting time required to cool the X-ray tube to perform CT imaging with the focus size, and
   wherein the display displays the waiting time.

4. The X-ray computed tomography imaging apparatus according to claim 3, wherein
   if the waiting time is not zero, the processing circuitry changes a value lowest in a priority among the resolution mode, application dose condition, and X-ray exposure time, and determines a focus size with which CT imaging is executable immediately.

5. The X-ray computed tomography imaging apparatus according to claim 1, further comprising
   a display configured to display the determined focus size.

* * * * *